United States Patent
Slatkine et al.

(10) Patent No.: US 7,886,747 B2
(45) Date of Patent: Feb. 15, 2011

(54) NON-PENETRATING FILTRATION SURGERY

(75) Inventors: Michael Slatkine, Herzelia (IL); Ehud Assia, Tel-Aviv (IL); Alex Harel, Savyon (IL); Adi Shargil, Bnei-Zion (IL)

(73) Assignee: I Optima Ltd., Ramat-Gan (IL)

( * ) Notice: Subject to any disclaimer, the term of this patent is extended or adjusted under 35 U.S.C. 154(b) by 1356 days.

(21) Appl. No.: 10/495,649

(22) PCT Filed: Nov. 3, 2002

(86) PCT No.: PCT/IL02/00872

§ 371 (c)(1),
(2), (4) Date: Dec. 16, 2004

(87) PCT Pub. No.: WO03/041623

PCT Pub. Date: May 22, 2003

(65) Prior Publication Data

US 2005/0096639 A1 May 5, 2005

Related U.S. Application Data

(63) Continuation-in-part of application No. 10/240,505, filed as application No. PCT/IL00/00263 on May 8, 2000, now Pat. No. 7,135,016.

(60) Provisional application No. 60/331,402, filed on Nov. 15, 2001.

(51) Int. Cl.
*A61B 19/00* (2006.01)

(52) U.S. Cl. .......................................... 128/898; 606/6

(58) Field of Classification Search .................. 606/4–6, 606/10–12, 17, 18; 607/88, 89, 91, 94; 128/898
See application file for complete search history.

(56) References Cited

U.S. PATENT DOCUMENTS

| | | | |
|---|---|---|---|
| 3,828,788 A | | 8/1974 | Krasnov et al. |
| 4,665,913 A | | 5/1987 | L'Esperance |
| 4,907,586 A | | 3/1990 | Bille et al. |
| 4,963,142 A | | 10/1990 | Loertscher |
| 5,098,426 A | | 3/1992 | Sklar et al. |
| 5,129,895 A | * | 7/1992 | Vassiliadis et al. ............. 606/6 |
| 5,364,390 A | | 11/1994 | Taboada et al. |
| 5,370,641 A | * | 12/1994 | O'Donnell, Jr. ................ 606/4 |
| 5,423,801 A | * | 6/1995 | Marshall et al. ................ 606/5 |
| 5,520,679 A | | 5/1996 | Lin |
| 5,529,076 A | | 6/1996 | Schachr |

(Continued)

FOREIGN PATENT DOCUMENTS

EP 0765648 4/1997

(Continued)

OTHER PUBLICATIONS

Assia et al. "Non-Penetrating Glaucoma Surgery Using the CO2 Laser: Experimental Studies in Human Cadaver Eyes", SPIE, 4245: 228-233, 2001.

(Continued)

*Primary Examiner*—Ahmed M Farah

(57) ABSTRACT

Apparatus for ophthalmic surgery, especially non-penetrating filtration surgery, comprising a laser source that ablates sclera tissue at steps of intermediate thickness. Optionally, the beam is scanned using a scanner and its results viewed using an ophthalmic microscope.

20 Claims, 7 Drawing Sheets

U.S. PATENT DOCUMENTS

| | | | |
|---|---|---|---|
| 5,549,598 A * | 8/1996 | O'Donnell, Jr. | 606/6 |
| 5,549,632 A | 8/1996 | Lai | |
| 5,620,435 A | 4/1997 | Belkin et al. | |
| 5,634,920 A | 6/1997 | Hohla | |
| 5,733,276 A | 3/1998 | Belkin | |
| 5,738,677 A | 4/1998 | Colvard et al. | |
| 5,782,822 A | 7/1998 | Telfair et al. | |
| 5,827,266 A | 10/1998 | Harel et al. | |
| 6,010,497 A | 1/2000 | Tang et al. | |
| 6,059,772 A | 5/2000 | Hsia et al. | |
| 6,159,202 A | 12/2000 | Sumiya et al. | |
| 6,220,247 B1 * | 4/2001 | Maldonado Bas | 128/898 |
| 6,241,721 B1 | 6/2001 | Cozean et al. | |
| 6,258,082 B1 | 7/2001 | Lin | |
| 6,263,879 B1 | 7/2001 | Lin | |
| RE37,504 E | 1/2002 | Lin | |
| 6,540,391 B2 | 4/2003 | Lanzetta et al. | |
| 7,135,016 B1 * | 11/2006 | Asia et al. | 606/5 |
| 2001/0029363 A1 | 10/2001 | Lin | |
| 2002/0026179 A1 | 2/2002 | Toh | |
| 2006/0106370 A1 * | 5/2006 | Baerveldt et al. | 606/4 |

FOREIGN PATENT DOCUMENTS

| | | |
|---|---|---|
| EP | 0 770 370 | 5/1997 |
| EP | 1138290 | 10/2001 |
| JP | 09-122168 | 5/1997 |
| WO | WO 98/55888 | 12/1998 |
| WO | WO 01/50969 | 7/2001 |

OTHER PUBLICATIONS

Barak et al. "Anterior Capsulotomy Using CO2 Laser", SPIE, 3246: 196-198, 1998.

Communication Pursuant to Article 96(2) EPC Dated Dec. 5, 2006 From the European Patent Office Re.: Application No. 02775192.4.

Internationa Preliminary Examination Report Dated Jun. 4, 2003 From the International Preliminary Examing Authority Re.: Application No. PCT/i100/00263.

Notice of Allowance Dated Mar. 2, 2006 From the US Patent and Trademark Office Re.: U.S. Appl. No. 10/240,505.

Office Action Dated Sep. 11, 2008 From the Israeli Patent Office Re.: Application No. 161936.

Official Action Dated Oct. 7, 2004 From the US Patent and Trademark Office Re.: U.S. Appl. No. 10/240,505.

Klink et al. "Erbium-YAG Laser-Assisted Preparation of Deep Sclerectomy", Graefe's Archive for Clinical and Experimental Ophthalmology, 238: 792-796, 2000.

Mueller et al. "Basic Laser Tissue Interaction", Lasers in Medical Science, 4(1): 7-15, Mar. 1989.

Assia, E. I. et al.; "Non-Penetrating Filtration Surgery Using the CO2 Laser—Experimental Studies in Human Cadaver Eyes" Abstracts for Annual Meeting at Neve Ilan Resort Hotel, Israel Society for Eye & Vision Research ; Mar. 16-17, 2000.

Belkin, M. et al.; "Clinical Evaluation of the Ex-Press Miniature Glaucoma Implant" Abstracts for Annual Meeting at Neve Ilan Resort Hotel, Israel Society for Eye & Vision Research; Mar. 16-17, 2000.

Belkin, M. et al.; "Non-Penetrating Trabeculectomy Using the $CO_2$ Laser in Rabbits;" Abstract No. 1419-B327; IOVS; vol. 40; No. 4; Mar. 15, 1999.

Summons to Attend Oral Proceedings Pursuant to Rule 115(1) EPC Dated Jun. 26, 2009 From the European Patent Office Re.: Application No. 00922836.2.

Translation of Decision of Rejection Dated Jun. 3, 2009 From the Japanese Patent Office Re.: Application No. 2003-543510.

European Search Report and the European Search Opinion Dated Jun. 11, 2010 From the European Patent Office Re. Application No. 10159723.5.

European Search Report and the European Search Opinion Dated Apr. 16, 2010 From the European Patent Office Re. Application No. 09178195.5.

Examination Report Dated Dec. 2, 2008 From the Government of India, Patent Office Re.: Application No. 1314/CHENP/2004.

Translation of Notification of Reasons of Rejection Dated Jan. 16, 2009 From the Japanese Patent Office Re.: Application No. 2001-581704.

Communication Pursuant to Rules 70(2) and 70a(2) EPC and Reference to Rule 39(1) EPC Dated Jul. 19, 2010 From the European Patent Office Re. Application No. 10159723.5.

International Preliminary Examination Report Dated Jun. 4, 2003 From the International Preliminary Examing Authority Re.: Application No. PCT/i100/00263.

Notification of Reasons of Rejection Dated Dec. 15, 2009 From the Japanese Patent Office Re.: Application No. 2001-581704 and Its Translation Into English.

Summons to Attend Oral Proceedings Pursuant to Rule 115(1) EPC Dated Aug. 7, 2009 From the European Patent Office Re.: Application No. 02775192.4.

Müller et al. "Basic Laser Tissue Interaction", Lasers in Medical Science, 4(1): 7-15, Mar. 1989.

* cited by examiner

NON-PENETRATING FILTRATION SURGERY

RELATED APPLICATIONS

The present application is a U.S. national application of PCT Application No. PCT/IL02/00872, filed on Nov. 3, 2002. This application is a continuation in part of PCT Application No. PCT/IL00/00263, filed on May 8, 2000, now U.S. application Ser. No. 10/240,505. This application also claims the benefit under §119(e) of U.S. Provisional Application No. 60/331,402, filed on Nov. 15, 2001. The disclosure of all of these applications are incorporated herein by reference.

FIELD OF THE INVENTION

The present invention is related to the field of Glaucoma treatment using laser ablation.

BACKGROUND OF THE INVENTION

Glaucoma is an optical neuropathy associated with increased intraocular pressure. The mechanism of the disease is not fully understood. However, the most effective therapy appears to be reducing the intraocular pressure, for example using medication or implants. Further damage to the optic nerve is thus prevented or reduced.

One procedure that has been suggested is non-penetrating trabeculectomy, in which a portion of the sclera overlying the Schlemm's canal is removed, allowing aqueous humor to leave the eye. It is desirable to remove only part of the thickness of the sclera, preventing penetration into the eye. However, this procedure is difficult to perform with a knife. Typically, the effect of the procedure can only be gauged after a while, since intra-ocular pressure is only measured after the procedure is completed. As the pressure of the knife causes trauma to the eye, the pressure is not usually measured until the eye has somewhat recovered, such as the next day. In laser based procedures, such as SLT and ALT, pressure is sometimes measured after the procedure is completed, to ensure that the intra-ocular pressure did not suddenly rise.

U.S. Pat. No. 5,370,641 to O'Donnell, the disclosure of which is incorporated herein by reference, describes using an Excimer laser or an Erbium laser to ablate the sclera overlying the Schlemm's canal and the trabecular meshwork thereby forming a porous membrane. The laser spot size and treatment area are not described. This patent states that when a sufficient amount of the corneoscleral bed is removed, aqueous humor comes through the remaining ultra-thin Schlemm's canal and trabecular meshwork and the energy of the laser is absorbed by the out-flowing humor, creating a self-regulating end point.

However, even though many years have passed since this patent was issued, the method taught in the patent has not found wide-spread use, in spite of a great need in the art of treating Glaucoma, a disease for which there is no completely satisfactory treatment. One possible reason is that the '641 patent uses lasers that remove very thin (micron sized) layers of material. Further, once even a weak percolation starts, the laser is only effective to remove the percolation, not further tissue, while at the same time possibly causing thermal damage to the underlying tissue. This thermal damage may be a cause of later scarring.

SUMMARY OF THE INVENTION

An aspect of some embodiments of the invention relates to apparatus for effecting and controlling a non-penetrating filtration procedure, using an ablation source that remove a layer of tissue of intermediate thickness, for example, between 5 and 30 microns. In an exemplary embodiment of the invention, the ablation source and parameters are selected so that the removal depth is smaller than a desired final membrane thickness but greater than a thickness of percolation which may be expected prior to the desired membrane thickness being achieved. In an exemplary embodiment of the invention, the ablation source is absorbed by the percolation. Optionally, the ablation parameters are selected so that the process of ablation is self-curtailed when the percolation is fast enough to create a layer the thickness of the ablation depth. In an exemplary embodiment of the invention, the ablation source is selected to have the flexibility to provide more than one meaningful ablation depth.

In an exemplary embodiment of the invention, the laser is a diode laser operating at 1.8 microns, a $^{13}C^{16}O_2$ isotope laser or an Erbium:YSGG laser. In contrast to Erbium:YAG lasers, for example, the above listed lasers have an ablation depth that is greater than the small ablation depth of 1-3 microns of the Erbium:YAG laser. This is also the percolation thickness which may be expected to exist, in many cases, long before the membrane is thin enough. While the thickness of the percolation is dependent on the time between pulses, practical reasons, such as laser pulse rate, thermal damage and shock wave damage potentially caused by the laser pulse transfer generally prevent the practical use of low (e.g., micron) ablation depth lasers such as the Excimer and Er:YAG for the application of ablation. It should be noted that in the field of skin resurfacing, the standard (non isotopic) $^{12}C^{16}O_2$ laser rules supreme. While this laser does have some degree of flexibility the minimum ablation depth (where a minimum of charring is produced) is about 30 to 50 microns, which may not be fine enough for some patients and/or protocols. In addition, it should be noted that unlike in skin applications, thermal damage to the membrane and/or other eye tissue does not heal as readily and is more likely to scar, for example due to the lack of underlying healing tissue.

In an exemplary embodiment of the invention, the apparatus includes a scanner for automatically scanning an area of the eye using a laser spot, thereby ablating over the entire area. Optionally, a continuous scan is used, with the laser beam on at all times. A potential advantage of using a scanner is the ability to provide a large total amount of energy to a large area of the eye using a relatively inexpensive laser and scanning the beam over the area. Optionally, a pulsed $^{13}C^{16}O_2$ laser such as an ultrapulse laser with a scanner, for example, a galvanometric scanner, is used.

Another potential advantage of using a scanner is that a uniform percolation profile (or another desired profile) may be achieved. Optionally, a uniform final tissue thickness is created by the ablation. Alternatively, different tissue types or areas may have different thickness, so that a uniform percolation is achieved. In some cases, the ablated sclera or cornea thickness will vary responsive to the underlying tissue. In some embodiments of the invention, the desired percolation rate is a factor that controls the process and/or ablation parameters.

In some embodiments of the invention, a reservoir is ablated in the sclera and/or cornea for collecting the percolating aqueous humor.

In one embodiment of the invention, the laser beam is optically combined with a visual system, using an optical combiner, to allow monitoring of the procedure. Optionally, the visual system is a ophthalmic microscope, for viewing the area of ablation by a physician performing the procedure. Alternatively or additionally, the visual system is an automatic vision system. Optionally, the optical combiner comprises a micro-manipulator, allowing the physician to change the laser aiming point and/or scan area. It is noted that standard micro-manipulators and beam combiners do not support an input from a spatially scanning laser beams.

An advantage of monitoring using a human or automatic visual system is that the ablation at a particular location on the eye can be stopped as soon as the aqueous humor starts percolating out, without requiring an optional self-limiting behavior of the a laser beam to take effect.

An aspect of some embodiments of the invention relates to using a sensor, for example, an automatic vision system for monitoring a non-penetrating filtration procedure. In one embodiment of the invention, the vision system detects percolation of liquid from the ablated sclera or cornea, thus identifying that ablation at the percolating point should be stopped. Optionally, this allows a greater degree of safety. Alternatively or additionally, the vision system controls the scanner (or laser) to reduce or eliminate the scanning of the laser at some points, while continuing the scanning at other points in the eye.

In an alternative embodiment of the invention, a pressure sensor is used to measure an intra-ocular pressure, during and/or after a procedure. The measurement may be, for example, continuous or intermittent. The measurement may be performed during pauses in the procedure and/or may be performed while the procedure continues. In some cases, for example, if the pressure goes down this may indicate a successful percolation. If the pressure does not go down enough, this may indicate that a larger area should be ablated. If the pressure goes down too much, possibly the procedure should be stopped at once. This sensor may be coupled to the system to operate automatically. For example, an input from the sensor may be used to automatically stop or change ablation parameters. Alternatively, the sensor is used to generate an alarm, through the ablation system or on its own (e.g., by setting a pressure at which to sound an alarm). Alternatively or additionally, the sensor is used manually, for example, with a physician entering new ablation parameters into the ablation system (e.g., using a suitable input) based on the pressure reading and/or entering pressure values which are interpreted by the ablation system to change its parameters.

Alternatively or additionally to using a pressure sensor, an ablation thickness sensor or a sclera thickness sensor is used to determine if ablation is to continue and/or under what parameters.

In an exemplary embodiment of the invention, the pressure sensor is a non-penetrating sensor that optionally contacts the outside of the eye. Alternatively, a penetrating pressure sensor is used, for example, as part of a system that penetrates the eye and controls the intra-ocular pressure by providing or removing fluid, as needed.

An aspect of some embodiments of the invention relates to an eye protector. In an exemplary embodiment, the eye protector prevents ablation by the laser outside of a predefined area, for example by physically blocking the laser light. Optionally, the eye protector is adhesive to the eye. Alternatively or additionally, the eye protector maintains open, during the procedure, one or more flaps formed in the eye. Alternatively or additionally, the eye protector is disposable.

There is thus provided in accordance with an exemplary embodiment of the invention, apparatus for ophthalmic surgery on an eye comprising:

a laser source that generates a laser beam, adapted to ablate a scleral tissue thickness of between 5 and 30 microns in a single shot; and an ophthalmicly effective position controller. Optionally, the apparatus comprises an ophthalmic microscope operative to view an eye during an ophthalmic procedure that uses said laser beam. Optionally, the apparatus comprises a monitor for displaying a view of said tissue removal viewed by said microscope. Alternatively or additionally, the apparatus comprises a beam combiner for combining a line of sight of said laser and said microscope.

In an exemplary embodiment of the invention, said position controller comprises an ophthalmic frame operative to fixing a relative position and angle of said laser source and an eye of a patient. Alternatively or additionally, said position controller comprises a scanner comprising an input for said laser beam and an output of a spatially scanned laser beam. Optionally, the apparatus comprises controlling circuitry that drives said scanner to remove tissue in a desired pattern on the eye. Optionally, the apparatus comprises a sensor which monitors an indication of progression of said surgery, on said eye, to produce a progression signal. Optionally, the apparatus comprises:

a camera which acquires an image of said tissue removal; and an image processor that processes said image. Alternatively or additionally, the apparatus comprises circuitry that uses said progression signal to generate an indication of the tissue removal state. Optionally, said circuitry uses said indication to close a control loop of said tissue removal. Alternatively or additionally, said indication of tissue removal state comprises an indication of the thickness of remaining tissue in the area of tissue removal. Alternatively or additionally, said indication of tissue removal state comprises an indication of a percolation rate through the remaining tissue in the area of tissue removal.

In an exemplary embodiment of the invention, said sensor measures an intra-ocular pressure. Alternatively or additionally, said sensor is a non-penetrating sensor. Alternatively or additionally, said sensor is a contact sensor.

In an exemplary embodiment of the invention, said controlling circuitry receives signals from said sensor.

In an exemplary embodiment of the invention, the apparatus comprises a user input, wherein said controlling circuitry is adapted to receive and interpret entries on said input as indicating signals from said sensor.

In an exemplary embodiment of the invention, the apparatus comprises a frame attached to said combiner, which frame blocks said laser beam from at least one part of said eye.

In an exemplary embodiment of the invention, said laser source comprises a $CO_2$ laser source.

In an exemplary embodiment of the invention, said laser source comprises an isotopic $^{13}C^{16}O_2$ laser source.

In an exemplary embodiment of the invention, said laser source comprises an Erbium:YSGG laser source.

In an exemplary embodiment of the invention, said laser source comprises a diode laser source operated at a wavelength near 1.8 microns.

In an exemplary embodiment of the invention, said laser source comprises a UV laser source.

In an exemplary embodiment of the invention, said laser source generates a second, visible wavelength, aiming beam aligned with said laser beam.

In an exemplary embodiment of the invention, said laser beam is a pulsed laser, each pulse being a single shot. Alternatively, said laser beam is a pulsed laser, a plurality of pulses being grouped as a single shot. Alternatively, said laser beam is a continuous laser that is artificially gated to generate shots.

There is also provided in accordance with an exemplary embodiment of the invention, a method of performing a non-penetrating filtration procedure, comprising:

opening a flap in an eye, overlying a Schlemm's canal of said eye;

forming a percolation zone adjacent said Schlemm's canal by ablation using a laser that ablates a tissue thickness of between 5 and 30 microns, each shot;

forming a reservoir in a sclera of said eye and in fluid connection with said percolation zone; and closing said flap. Optionally, forming a percolation zone comprises cleaning away charred tissue from said percolation zone. Alternatively or additionally, the method comprises forming by automatic scanning with a laser. Optionally, automatic scanning with a laser comprises automatically controlling at least one parameter of the scanning responsive to an effect of the laser on the tissue.

In an exemplary embodiment of the invention, said laser is a $CO_2$ laser. Alternatively, said laser is a $^{13}C^{16}O_2$ laser. Alternatively, said laser is an Er:YSGG laser. Alternatively, said laser is a diode laser operated near 1.8 microns wavelength.

In an exemplary embodiment of the invention, the method comprises placing a protective sticker on said eye prior to forming said percolation zone, said protective sticker having a spatial window that admits a wavelength of said laser and a body that block said wavelength from parts of the eye other than an area to be ablated.

There is also provided in accordance with an exemplary embodiment of the invention, a method of performing a non-penetrating filtration procedure, comprising:

forming a percolation zone adjacent a Schlemm's canal of an eye measuring an intra-ocular pressure of said eye in response to said forming a percolation zone; and modifying parameters of said forming in response to said measuring.

BRIEF DESCRIPTION OF THE FIGURES

Exemplary, non-limiting embodiments of the invention will be described below, with reference to the following figures, in which the same elements are marked with the same reference numbers in different figures.

DETAILED DESCRIPTION OF SOME EMBODIMENTS

Figure 1:
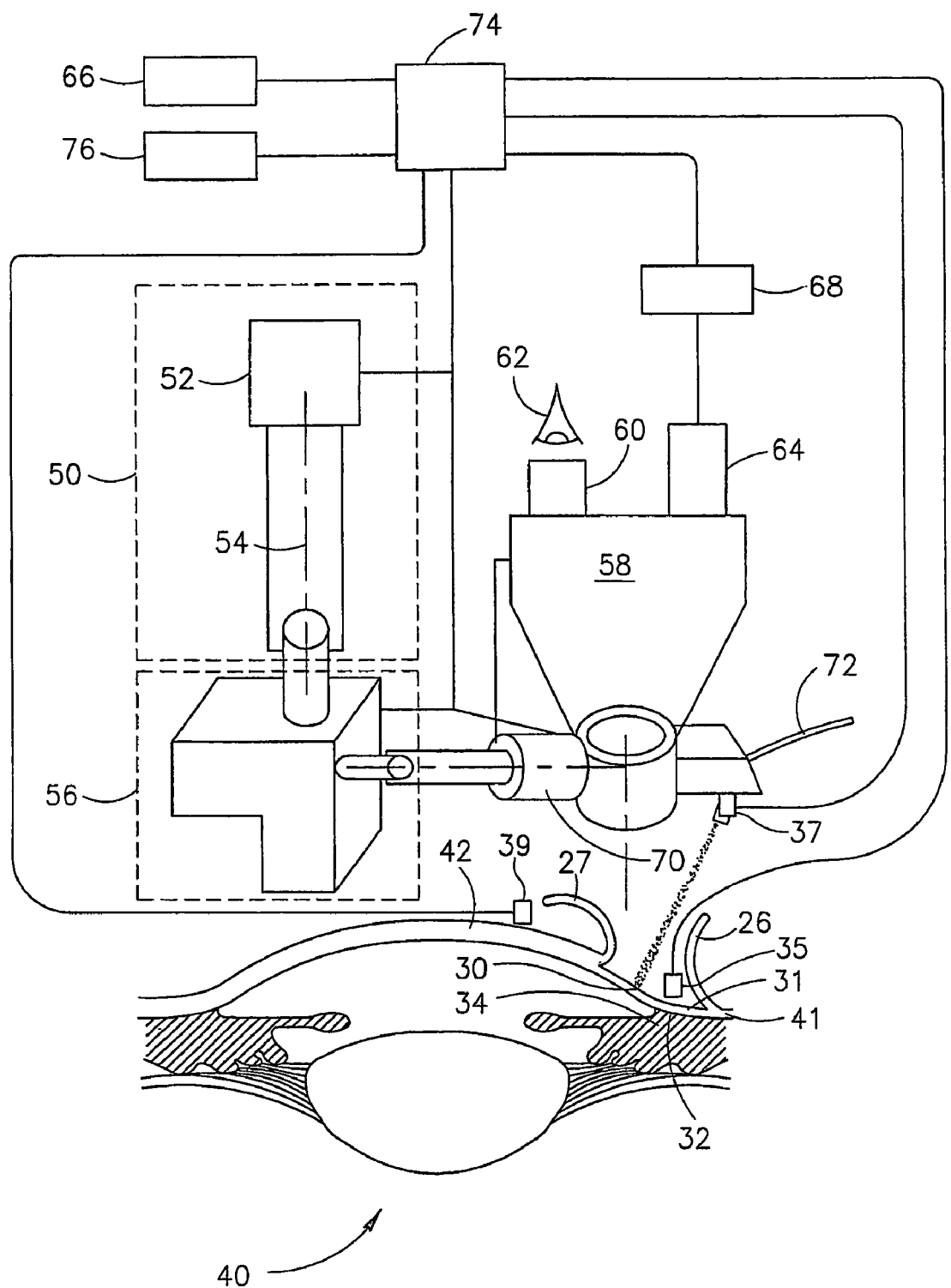
FIG. 1 is a schematic illustration of an exemplary ophthalmologic ablation system, during a non-penetrating filtration procedure in accordance with an exemplary embodiment of the invention.

FIG. 1 is a schematic illustration of an exemplary ophthalmologic ablation system 50, during a non-penetrating filtration procedure in accordance with an exemplary embodiment of the invention.

Referring first to an eye 40, an exemplary filtration procedure using system 50 comprises ablating parts of an area 31 of a sclera 41 and/or a cornea 42 in an area 30. Some of the ablation is directed to those areas overlying a Schlemm's canal 34 and/or trabecular meshwork 32. The size of area 30 is exaggerated in FIG. 1, as in many procedures, area 30 is significantly smaller than area 31 and may comprise substantially only the boundary area between cornea 42 and sclera 41 that overlies the Schlemm's canal. In some procedures, however, a larger portion of the cornea may be ablated. Optionally, a scanner is used to scan a laser spot over an area of the sclera larger than the spot. A more detailed description of an exemplary filtration procedure and an exemplary scanner is provided below. Also shown are optional sensors 35, 37 and/or 39, described below.

The thickness of sclera tissue at area 30 prior to ablation is, for example, 1 mm. The desired thickness of the sclera after ablation is, for example, between 10 microns and 50 microns. It should be noted that it is desired that a complete membrane of sclera tissue be maintained, to reduce complications caused by entering the eye itself.

Laser ablation operates by light being absorbed by tissues in a thin layer, for example between 1 and 50 microns thick and the light causing heating of the tissue, so that the absorbing tissue explodes. This explosion can also cause (generally unwanted) damage by means of a shockwave produced by the explosion or by heat that is absorbed by underlying and/or adjacent tissue. When the membrane is thin enough, fluid percolates through the membrane and covers it. This fluid is generally very similar to the sclera tissue, especially with regard to optical absorption and heat dissipation properties. Thus, the fluid ablates in much the same way and parameters as sclera tissue. As can be expected, each type of laser wavelength has different interaction parameters with the sclera tissue and has further functional limitations caused by the physical limitations of the laser, for example commercially viable power level and pulse rate.

It has now been determined that different types of lasers have different utilities when used for ablation of the sclera and for non-penetration filtration. In particular, two properties of the laser may be of interest. First, the depth of ablation, which determines how large a thickness is ablated at one time and, second, the matching between the fluid ablation and the sclera ablation.

Figure 2A:
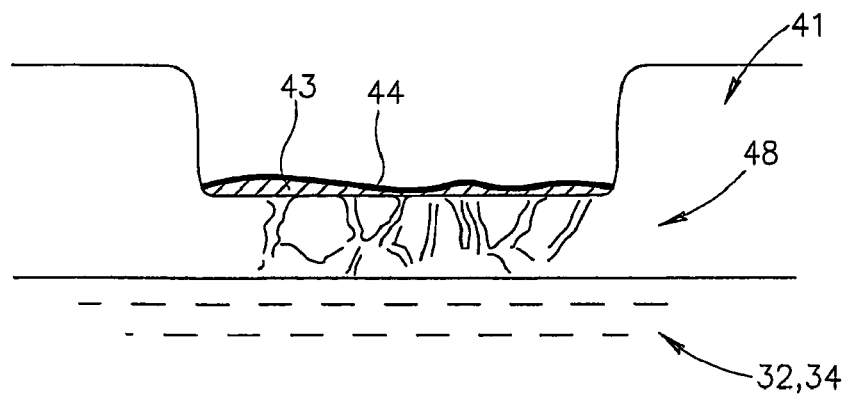
FIGS. 2A-2C illustrate the absorption of laser energy by sclera tissue, for three different types of laser source.
Figure 2B:
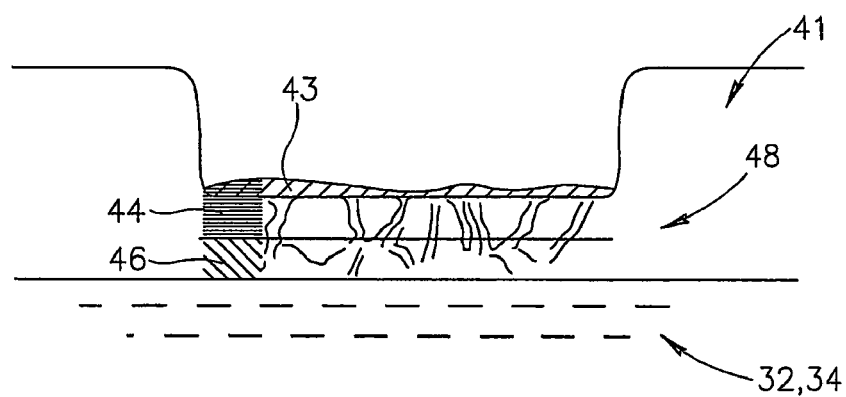
Figure 2C:
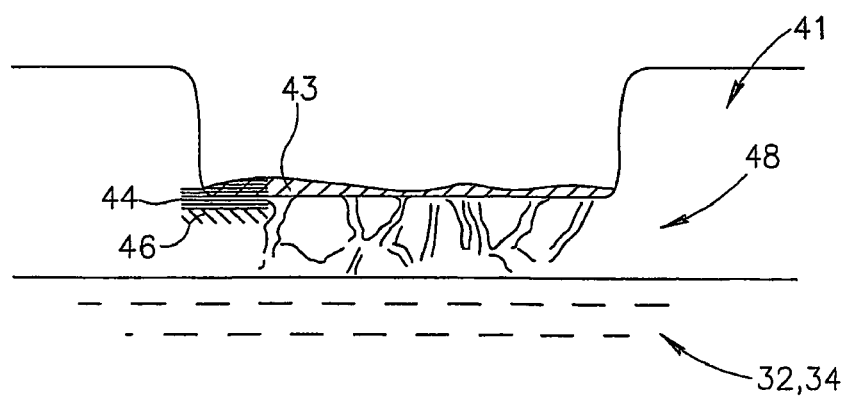

In some cases, an interesting result of these two properties, self-limiting of ablation, can be achieved. For example, if a laser has a given ablation depth and the fluid has the same ablation properties as the sclera and the local pulse rate of the laser is low enough to allow fluid to percolate to the ablation thickness, repeated laser pulses will only remove (the self renewing) fluid and not further ablate the sclera. In some cases, however, this self-limiting behavior can be self defeating or meaningless. FIGS. 2A-2C show the effects of various types of laser on sclera tissue.

FIG. 2A shows the situation where a highly absorbed laser, such as Erbium:YAG is used. Reference 43 indicates the amount of fluid that percolated through a membrane 48 since the laser pulse. Reference 44 indicates the area that can be ablated by a single Erbium:YAG laser pulse. As can be seen, the ablation of membrane 48 cannot continue if fluid 43 percolates faster than the pulse rate. The effective pulse rate is moreover limited by the damage caused by shockwave of the laser and by the laser itself which has a limited pulse rate. If scanning is desired, this further limits the effective pulse rate of the laser, in as much as percolation from adjoining areas may also cover the ablated area.

FIG. 2B shows the situation where a low absorption laser is used, for example, a $^{12}C^{16}O_2$ laser. This laser is characterized by a large ablation depth 44 (e.g., 30-50 microns as opposed to 1-3 microns of an Erbium:YAG laser) and also a large thermal damage depth 46. Thus, in the configuration shown, the small amount of percolation does not prevent a large thickness of sclera from being ablated. However, the remaining sclera is likely to be thermally damaged. Also, it is difficult to fine tune the exact thickness of membrane 48, in as much as the depth of ablation is so large. Thus, the percolation rate, which is dependent on the thickness of membrane 48, is more difficult to exactly achieve. In fact, the self-limiting point may be skipped by the laser inadvertently ablating clear through the sclera. In many cases, however, even such rough approximation may be good enough, for example, by ablating different thickness of membrane over different parts of the eye, so that the total effective (e.g., averaged) percolation rate is as desired, while taking care to not over-ablate the sclera and penetrate the eye. Alternatively or additionally, the local pulse rate may be selected to be low enough (e.g., by modifying the pulse rate and/or scanning pattern) so that a sufficiently thick layer of fluid 43 percolates and serves to control the amount of actual sclera tissue ablated.

FIG. 2C shows the situation where an intermediate absorption laser is used, for example, an isotopic $^{13}C^{16}O_2$ laser, an Erbium:YSGG or a diode laser at 1.8 microns wavelength. The thickness of ablation and of thermal damage is relatively small, especially relative to a final desired membrane thickness, but still greater than percolation that occurs when the membrane is not at its target thickness. It should be noted that there may be a variation in percolation rate between patients and/or intra-ocular eye pressures, so that even if a same membrane thickness and/or percolation properties are desired, different fluid percolation rates may be observed during the procedure.

Figure 2D:
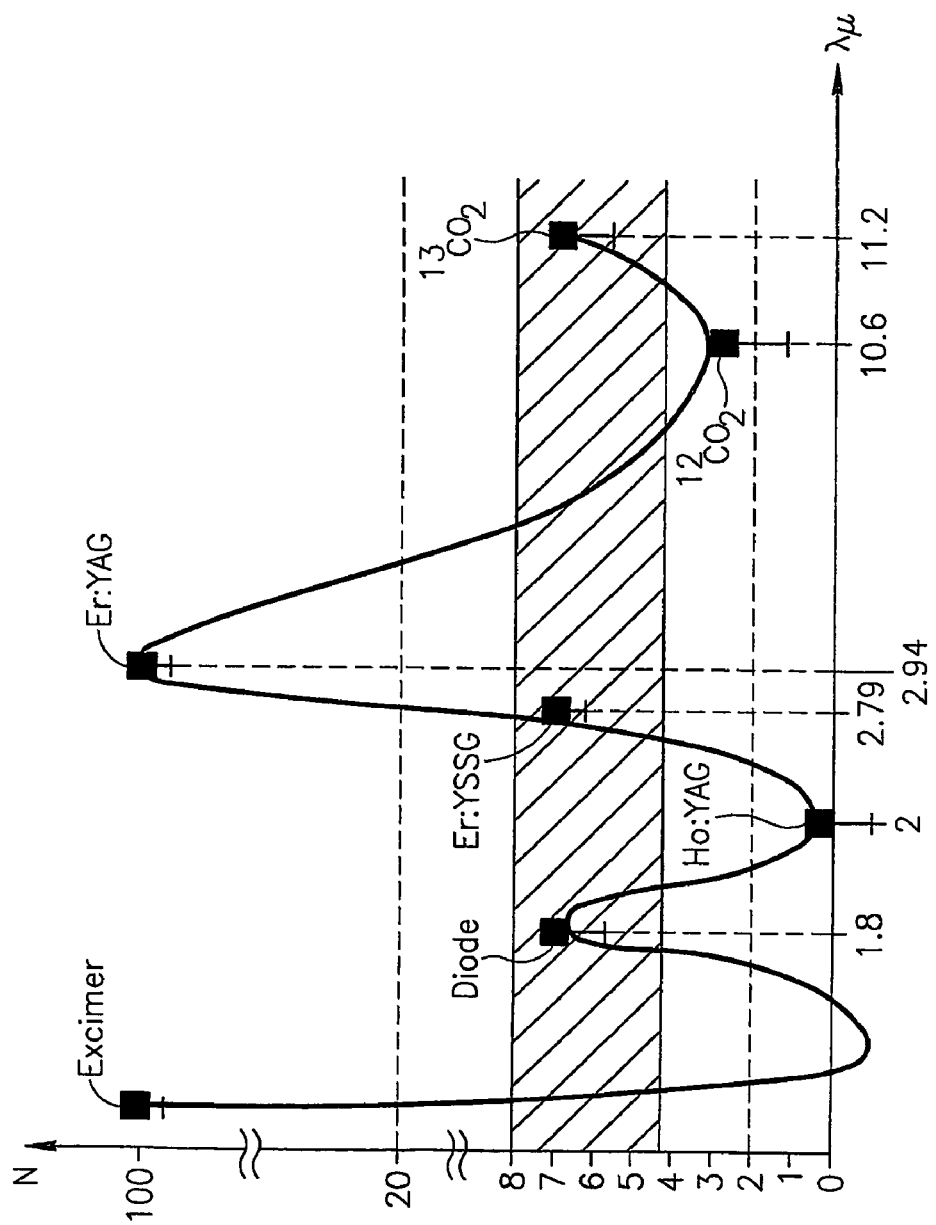
FIG. 2D is a graph showing the relative utility of lasers for sclera surgery, in accordance with an exemplary embodiment of the invention.

FIG. 2D is a graph showing the relative utility of lasers for sclera surgery, in accordance with an exemplary embodiment of the invention the different lasers are compared using a unit N which indicates thickness of membrane 48 in units of minimum ablation thickness of the laser. The thickness of membrane 48 is taken to be 100 microns, thus, N=(100 microns/ablation thickness). If a different thickness is selected, different values of N will be generated. A more exact presentation of N and the ablation depth (based on a minimum or typical penetration depth that provided effective ablation) is shown in a table below. The one sided "error" bars indicate the depth of thermal damage to be expected. Two bands are marked on the figure. The shaded band indicates a range of values for N which apparently afford control while allowing a desired ablation to be performed. The dotted lines enclose a wider band where control is marginal but may be suitable for various applications. In general, as N is larger, finer control can be achieved, but procedure time is longer and is in danger of being limited by non-final percolation. As N is smaller, less control but surer ablation can be achieved. For some lasers, it is possible to control the penetration depth by modifying the pulse duration and/or the energy of the pulse. However, many lasers are limited by the physical properties of the laser and/or the degree of control is not sufficient to allow a laser that is not useful to become useful.

As can be appreciated, these indications are not absolute. For example, if the desired membrane thickness is greater, lasers with a currently low N may become more useful. Lasers with a high N, however, suffer from being self limiting when there is percolation, thus, to be effective, the laser must be able to provide multiple pulses in the time it takes for percolation the thickness of the ablation depth to occur, if this percolation is not the desired final effect. Also, some method of preventing damage from shockwave and other artifacts may be required. Thus, other useful values of N (for a 100 micron thickness) are below 50, 20, 10 and 6 and/or above 2, 3, 4, 5, 7 and 10. In general, a useful value of N for any thickness may depend on the precision desired in setting the thickness, so the above listed possibly useful values of N may apply to an N calculated using a different membrane thickness.

As can be seen, Erbium:YAG and Excimer lasers have too small an ablation thickness, while $^{12}C^{16}O_2$ is marginal and Ho:YAG has too large an ablation thickness. Diode lasers operated at 1.8 micron wavelength, Erbium:YSGG and isotopic $^{13}C^{16}O_2$ operated at 11.2 microns wavelength have an intermediate ablation thickness which allows for freedom in manipulating the thickness (e.g., by increasing the energy) and more exact approximation of the final membrane thickness, even under conditions of partial percolation. Other lasers may be used as well, if they have spectral characteristics (and/or absorbency characteristics) that match the areas and lines shown in FIG. 2D.

| Laser Type | Penetration depth in water (1/e) = approximate ablation depth | N (for thickness of 100 microns) |
| --- | --- | --- |
| Excimer | 1 micron | 100 |
| Diode at 1.8 micron | 20 microns | 5 |
| Holmium:YAG | 100-200 microns | 1-0.5 |
| Er:YSGG | 15 micron | 7 |
| Er:YAG | 1-3 micron | 100-30 |
| $^{12}C^{16}O_2$ | 30-50 micron | 2-3 |
| $^{13}C^{16}O_2$ | 15 micron | 7 |

Alternatively, a laser may be selected that has a low absorption in the percolating fluid, and an intermediate or high absorption in the sclera tissue. However, this laser may not have the desired self-limiting effect. Alternatively, a combination of laser wavelengths may be used.

The laser source is shown in FIG. 1 as a laser source 52.

The type of interaction of the laser (or other light) with the eye is typically that of ablation, especially low-char ablation. However, other tissue removing interactions may be used as well, for example, vaporization and coagulation (and then optionally removal of the damaged tissue).

Optionally, source 52 also generates an aiming laser beam (not shown), having a low power and/or being visible. The aiming beam is optionally coaxial with ablation beam 54. This aiming beam may be formed by a separate laser boresighted with beam 54.

In one embodiment of the invention, laser beam 54 has a spot size smaller than the size of area 30 that is actually ablated. Beam 54 is optionally scanned over area 30 using a scanner 56, for example a mechanical, electro-optical or acusto-optical scanner. An exemplary scanner is described in greater detail below.

In some embodiments of the invention, the procedure is monitored through an ophthalmic microscope 58 or other suitable optical instrument. In one embodiment of the invention, a human viewer 62 views area 30 though an eyepiece 60 of microscope 58. Alternatively or additionally, the procedure is imaged using an imager 64, such as a CCD camera.

In an exemplary embodiment of the invention, beam 54 (and/or optional the optional aiming beam) is optically combined with the line of sight of microscope 58 and/or that of imager 64, using a beam combiner 70. Optionally, combiner 70 comprises a micro-manipulator, allowing the relative location of beams 54 and the line of sight of microscope 58 to be modified. Various types of micro-manipulators may be used, with a particular one being described below. In an exemplary embodiment, a joy stick 72 is provided on beam combiner 70 to control the relative lines of sight.

Unlike standard beam-combiners for ophthalmic use, combiner 70 is expected to receive a scanning beam, rather than a point source. Thus, the optics of combiner 70 are optionally designed to correctly aim the beam over a significant range of beam positions, such as ±2, ±4 or ±5 mm off center of the micro-manipulator input axis.

The image (or image sequence) acquired by imager 64 may be used in various ways. In one embodiment of the invention, the acquired image may be displayed, for example using a display 66. Alternatively or additionally, the acquired image is recorded. Alternatively or additionally, the acquired image is analyzed using an image processor 68. In some embodiments, the image and/or control parameters are transmitted to a remote location, such as using an Internet or other communication network.

In some embodiments of the invention, the image analysis is used to detect the percolation of aqueous humor. Alternatively or additionally, the image processing confirms that ablation beam 54 (or the aiming beam) are within a designated safety area. Alternatively or additionally, the image processing detects the depth of ablation, for example using stereoscopic images, by shadow analysis and/or by virtue of thin tissue being more transparent. The thickness of the tissue may be then determined, for example, by shining a strong light into the eye and measuring the relative or absolute amount of light exiting through the ablated tissue. Optionally, dye is provided into the eye, for example using iontophoresis (or injection) and the degree of percolation is determined by viewing the color intensity of the percolating aqueous humor.

The detected percolation may be used to provide feedback to the treating physician, for example using display 66 or via an audio alarm (not shown). Alternatively or additionally, laser 52 may be shut off or beam 54 blocked, for example at scanner 56 or combiner 70. Alternatively or additionally, the image processing results may be used to complete a control loop, such as by controlling the scanning parameters of scanner 56.

In some cases, the laser beam may inadvertently penetrate into the eyeball. Optionally, such penetration is detected based on a flow rate of aqueous humor from the eye (which is a typically higher rate than that provided by percolation). Optionally, the procedure may be completed as a penetrating filtration procedure. Alternatively or additionally, a penetration is planned at at least one part of the eye. Optionally, the scanner is controlled to congeal and/or scar the tissue at or near the penetration area.

In one embodiment of the invention, a controller 74 is provided to receive the image processing results and apply suitable control to laser source 52, scanner 56, combiner 70. Alternatively or additionally, controller 74 is used for processing and displaying of data and/or for receiving input from the treating physician, such as procedure parameters. An suitable input device 76 may be provided.

Figure 3A:
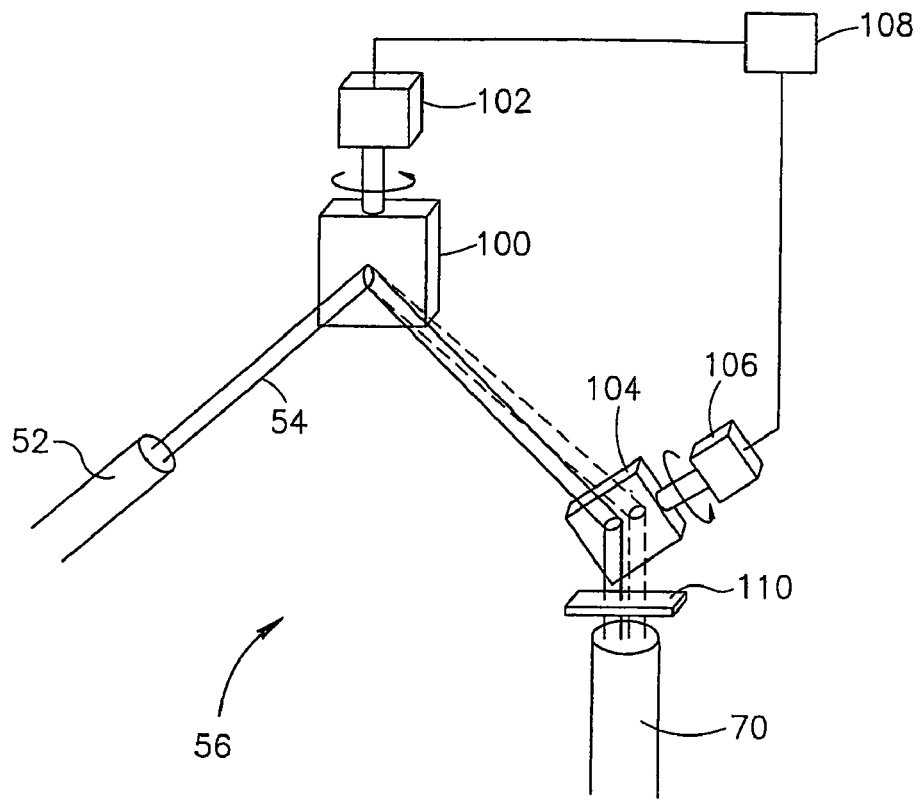
FIG. 3A is a schematic illustration of an exemplary scanner suitable for the system of FIG. 1.

FIG. 3A is a schematic illustration of an exemplary scanner 56 suitable for system 50. A beam 54 from laser source 52 is scanned in a first axis by a mirror 100, powered by a motor 102. A second mirror 104, powered by a second motor 106 scans the beam in another, optionally orthogonal axis. The two mirrors may be controlled by a scanning controller 108. The scanning is optionally continuous over a defined scanned area. In some embodiments, a same scanner may be used for scanning different sized and shaped areas. A beam attenuator 110 is optionally provided to selectively attenuate beam 54, for particular scanned locations in area 30 and 31 (FIG. 1). Attenuator 110 may be a one cell attenuator or it may be a spatial modulator. It should be noted that many different scanner designs can be used to generate a scanned beam, for example scanners using rotating prisms and acusto-optical scanners.

Additional potential advantages of a scanner which may be realized in some embodiments of the invention, include:

(a) limiting the laser and/or heat damage from nearby areas;

(b) providing depth control of the ablation in different parts of the eye;

(c) providing percolation rate control in different parts of the eye;

(d) when uniform ablation is desired, allowing selection of uniform depth or uniform tissue thickness;

(e) varying the scanning speed, intensity, pulse rate and/or other parameters based on the tissue type. Controller 74 may be used to simultaneously control laser 52 and scanner 56 to achieve various desired laser effects; and/or (f) controlling the local pulse rate to match the actual pulse rate of the laser with the local percolation rate and a desired percolation rate at which the procedure should be self-limiting.

Figure 3B:
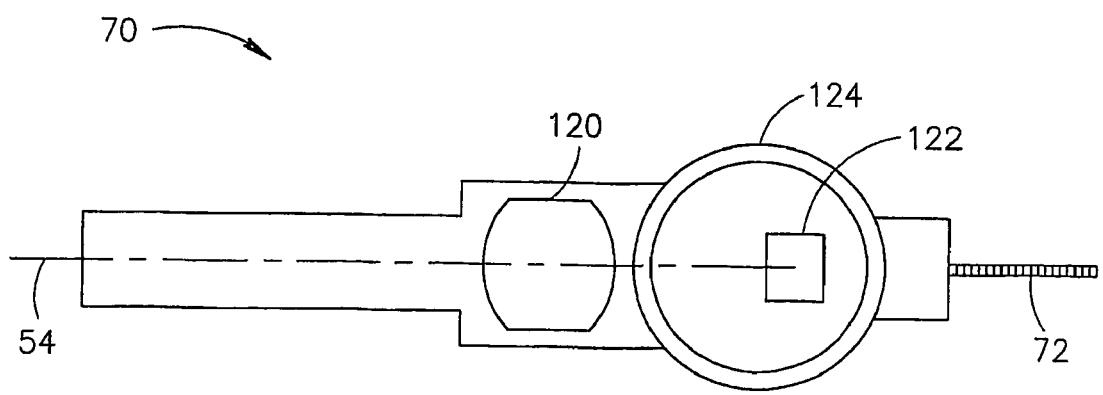
FIG. 3B is a schematic illustration of an exemplary micro manipulator for the system of FIG. 1, in accordance with an exemplary embodiment of the invention.

FIG. 3B is a schematic illustration of an exemplary combiner/micro-manipulator 70 for system 50, in accordance with one embodiment of the invention. As noted above, in some embodiments of the invention the input beam is scanned, rather than being restricted to a single spatial location. Thus, combiner 70 is optionally designed to properly combine the beam with the line of sight of microscope 58 over an expected range of off-axis positions of the scanning beam.

As shown in FIG. 3B, a beam 54 enters combiner 70 and is optically processed by an optical system 120, which system controls the focusing of beam 54, so that it will be focused at areas 30 and 31, as required. In one embodiment of the invention, optical system 120 is configured and/or controlled so that beam 54 has the same focal plane as microscope 58. As will be described below, this can be achieved manually or automatically.

The optical path of microscope 58 may be delimited by an enclosing ring 124.

Beam 54 is combined with the optical path of microscope 58, using a beam combining element 122, for example a mirror that is transparent or semi-transparent to visible light and reflective for infra-red (or the wavelength of the laser). In an exemplary embodiment of the invention, a joy-stick 72 or other input means is provided for rotating beam combiner 122, so that the relative placement of laser beam 54 and the viewing field of microscope 58 can be controlled. Alternatively, the scanning area is defined and/or moved using scanner 56, which may require a larger and/or wider angle beam combiner to be provided. Alternatively or additionally, scanner 56 is provided as a single unit integral with combiner 70.

Figure 4:
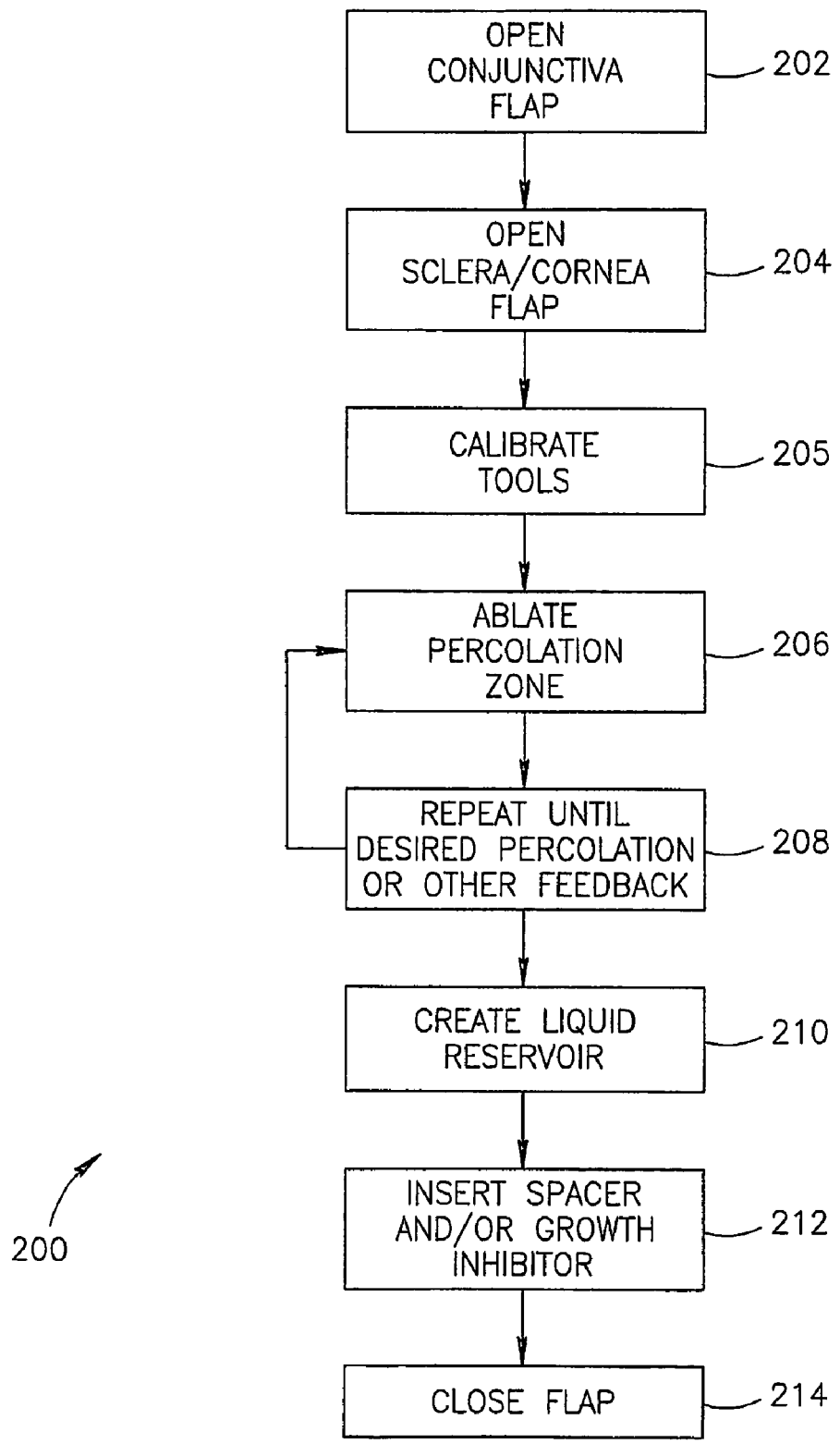
FIG. 4 is a flowchart of a method of non-penetrating filtration, in accordance with an exemplary embodiment of the invention.

FIG. 4 is a flowchart 200 of a method of non-penetrating filtration, in accordance with an exemplary embodiment of the invention. First, at 202, a flap 26 (FIG. 1) is formed in the conjunctiva of the eye. At 204, a flap is formed in the sclera 41 and cornea 42. Such flaps may be formed using any method known in the art, including using a scalpel, a laser and/or a dedicated cutting tool.

Figure 5:
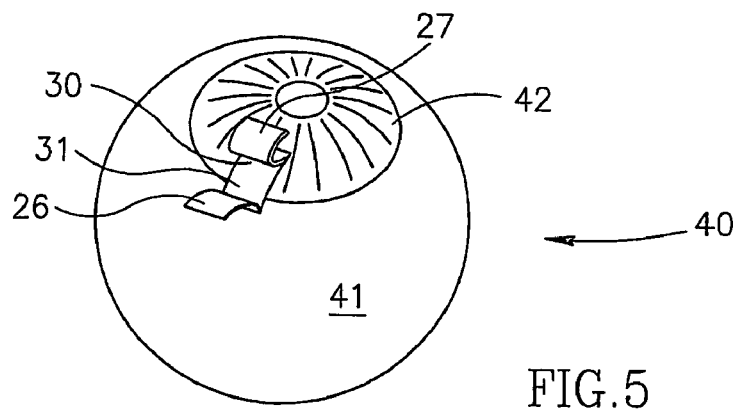
FIG. 5 is a perspective view of an eye showing an exposed ablation area, in accordance with an exemplary embodiment of the invention.

FIG. 5 is a perspective view of eye 40 showing an exposed ablation area 30 and 31, in accordance with an exemplary embodiment of the invention. In one embodiment of the invention, the flaps are opened so that they unroll in different directions. Thus, when the flaps are closed, the tip of one flap is under the base of the other flaps. This may provide a stronger seal. In the embodiment shown, the two flaps open in opposite directions, however, other angular relationships may be provided, for example an orthogonal relationship. Alternatively or additionally, the tip of sclera flap 27 is over sclera 41, for example, so that any swelling or inflammation will be less likely to affect the lens. Alternatively, the tip of flap 27 is over cornea 42 or, alternatively, over the boundary between the sclera and cornea.

At 205, the tools to be used are calibrated for the ablation area. In some embodiments, the tools are calibrated before the start of the procedure and/or periodically recalibrated during the procedure. Exemplary calibrations include: beam intensity, scanner/combiner alignment and/or laser focal plane. A laser focal plane calibration may be performed in conjunction with setting the microscope focal plane. Alternatively or additionally, a flexible focal distance combiner is used, which includes lens and/or other optical elements for varying the focal distance.

The target area may be shown, for example as a marking on mirror 122 (FIG. 3B). Alternatively or additionally, a computer display may be provided showing an image of the eye and an estimated or imaged position of the laser beam. In some embodiments, a computer generated display showing, for example, scanning parameters, is combined with microscope 58, so viewer 62 can view the display via the microscope.

Depending on the particular implementation, microscope 58 and/or combiner 70 (which may be an integral unit with microscope 58), may or may not be in contact with eye 40 and/or ablated areas 30 and 31.

As will be described below, in an exemplary embodiment of the invention, both a percolation zone 220 (FIG. 6 below) for allowing percolation of the aqueous humor and a reservoir zone 222 (FIG. 6 below) for storing the up-welling humor until it is absorbed, may be formed. They may be formed with a same scanning setting, as part of a same scan, or separately. In other embodiments, only a percolation zone is formed. Typically, these zones are covered by a tissue flap when the procedure is completed.

At 206, a percolation zone 220 is ablated in area 30 overlying Schlemm canal 34 and trabecular meshwork 32. If the aqueous humor does not percolate (208) the ablation step is repeated. In one embodiment of the invention, once a percolation is detected or a minimal percolation rate is detected (both of which may be manually or automatically detected), the ablation is stopped. In another embodiment of the invention, ablation is stopped or slowed down at points where percolation is detected, but continued at other parts of area 30 and/or area 31. A minimal percolation zone may be defined, which is smaller than the actual ablated area of area 30. Thus, the ablation is closed circuit, i.e., iterative, or open circuit ablation can be practiced as well, at least for the reservoir, for example based on predefined laser beam settings.

Typically, the tissue in area 30 has a varying thickness, by ablating more at areas where there is less percolation, a uniformly thin filter area may be defined. Alternatively, a uniform (or other profile) percolation distribution can be achieved. Also, percolation-adapted ablation allows a matching of the scanning parameters to the tissue laser sensitivity. One or more of the following scanning parameters may be varied over the ablation area, to control the ablation:

(a) Spot size. A larger spot size provides a lower resolution and less energy per unit area. In some embodiments, non-circular spots are used, for example, elliptical, triangular, hexagonal and rectangular. Alternatively or additionally, a spot pattern may be provided. Such a pattern may be continuous, for example Gaussian or uniform, or discrete, for example, checkerboard. Exemplary circular spot sizes are between 0.1 mm and 1 mm, for example 0.8 mm.

(b) Dwell time. By varying the scanning speed, more energy can be deposited at locations that are not yet percolating and less energy at locations where no further ablation is desired. An exemplary dwell time is between 100 μs and 1000 ms, for example 400 μs.

(c) Beam intensity. This may be controlled, for example, by modulating the laser source or using attenuator 110, or another attenuator (uniform or spatially modulating) elsewhere along the optical path. The attenuators may selectively attenuate only the ablating beam (and not the optional aiming beam) for example having frequency selective properties or being having a suitable physical location. In some cases, the beam may be turned off for part of the scan. An exemplary source beam intensity is between 5 W and 15 W. The actual intensity that should be delivered to the eye can depend on various parameters, for example, the dwell time (and spot size), the age of the eye tissue, and the type of effect desired, e.g., ablation or coagulation. In particular, increasing the beam intensity can increase the thickness of ablation.

(d) Beam location and scan pattern. In some embodiments, the beam scans the entire area, regardless of the effects of the beam. Alternatively, the beam may skip certain location and/or change the scan area definitions, on the fly, to match the percolating zones and/or required ablations.

(e) Scan path. In some embodiments, the scan path is selected so that there will be sufficient time to detect percolation at a location, between repeated ablations of the location. Alternatively or additionally, the scan path may be changed responsive to the initiation of percolation at some locations in the area. Optionally, the scan path overlaps itself, for example 10%. An exemplary scan path is by rows. Optionally, the scanning is interleaved, with a greater separation between rows. The row direction may reverse itself every row.

(f) Scan shape. Various scan shapes may be used, to achieve variously shaped percolation and/or reservoir shapes.

(g) Laser pulse parameters, such as pulse length, pulse envelope and pulse repetition rate. In some embodiments, a pulsed laser is used. The laser may generate a pulsed beam or a continuous pulsed beam may be further temporally modulated. In one exemplary embodiment, a CW laser is used and modulated to have pulses between 1 μs and 1 ms and a repetition between 1 Hz and 1 kHz. Alternatively, a continuous beam is provided at the eye. In a particular example, pulse duration is reduced, in order to reduce thermal damage.

(h) Local Pulse Rate. This is a composite of several parameters and defines the rate at which laser pulses will contact a certain area, thus also defining the time for percolation between pulses. By matching the local pulse rate to a desired percolation rate, the thickness of membrane 48 can be set or at least more closely approximated.

Alternatively or additionally to detection percolation using image processor 68, other feedback mechanisms may be used to control ablation, set ablation parameters and/or to provide alarm signals. Image processor 68 is optionally used to detect the thickness of the sclera and/or the depth of ablation. Several depth and distance measuring methods are known in the art, for example, using stereoscopic imaging, or by detecting shadows or changes in patterns of light that are projected from a side light (not shown). Alternatively or additionally, an optional dedicated sensor 37 (FIG. 1) is used, for example, for detecting percolation or measuring the thickness of the sclera or the depth of ablation, for example, optically or using ultrasonic reflection. A thickness sensor may also be used prior to the procedure, for example for mapping (e.g., to set ablation parameters in general or for different locations).

Alternatively or additionally, an optional contact sensor 35 (FIG. 1) is used to measure the sclera thickness, for example timing ultrasonic reflection from the aqueous humor of the eye. Alternatively or additionally, sensor 35 detects percolation (e.g., by detecting flow or moisture) and is located at an area which is not ablated. Optionally, the contact sensor is manually positioned so that the laser radiation does not hit it.

Alternatively or additionally to directly monitoring the ablation or the percolation, an optional sensor 39 (FIG. 1) may be used for monitoring the pressure in eye 40. Various types of such pressure sensors may be used, for example sensors which require applying pressure to the eye. Possibly, such sensors did not find use during surgery in previous times, due to fears of a possible interaction between such pressure (which may be deforming) and the delicacy of the procedure or the forcing of fluid from the eye. A potential advantage in accordance with an exemplary embodiment of the invention is the ability to receive feedback in real-time or near real-time on the effect of a part of the procedure, so that a more finely tuned effect on intra-ocular may be achieved.

When percolation is achieved, it is expected that the intra-ocular pressure will go down. However, after a time, the pressure may go up, stay steady, go down or oscillate for a while. The time until a steady pressure is achieved may be as long as several weeks or as short as a few minutes. However, it is expected that for some situations (e.g., initial pressure, type of ablation pattern, speed of response, degree of response) the behavior of the pressure can be estimated. Optionally, different changes in pressure profiles are stored and are used to identify the degree of percolation under different conditions (e.g., by accumulating a database of profiles and results). In an exemplary embodiment of the invention, two types of pressure reductions are distinguished, an immediate pressure reduction and a long term pressure reduction. Thus, for example, when percolation first occurs, the pressure is expected to go down to a lower level. This distinction, may, in some cases, be a simple modeling of an exponential decrease in pressure. In some cases, for example, the procedure is stopped when a reduced pressure 16 mm is achieved, even though a final expected and desired pressure is 12 mm. In other cases, the procedure may be stopped at 12 mm, and the pressure will then climb up to 16 mm, for a steady state final pressure. Optionally, detection of intra-ocular pressure reduction is used to automatically modify ablation parameters and/or to stop ablation. For example, the ablation pattern area may be reduced if pressure reduction is found. Alternatively, if a pressure reduction is not sufficient, the ablation pattern may be enlarged and/or pulse or scanning parameters (e.g., as described herein) changed. In a simple case, changes in pressure are used to decide if to stop the procedure.

The input from the sensor (or imaging system) may be used manually or automatically, depending on the implementation. For example, controller 74 may analyze and respond to input form such sensors automatically. Alternatively or additionally, a user reads the sensor readings and inputs new parameters into controller 74, for example using input 76. Alternatively or additionally, a user enters the sensor reading into the input and controller 74 analyses the input to determine a response. One potential advantage of such user intermediate activity is that there is no need to electrically couple the sensor to the ablation system and any existing sensor may be used.

Alternatively or additionally to storing pressure profiles, ablation rate profiles may be stored, with the understanding that as percolation initiates and processes, the ablation rate will go down. Such ablation profiles (e.g., thickness profiles) may be used to assess the progression of the procedure and/or to indicate alarm conditions.

At 210, reservoir 222 (FIG. 6) is optionally created. Instead of using percolation to detect the reservoir depth, it may be estimated based on the laser energy deposition or it may be determined using image processor 68. In some embodiments, reservoir 222 is created while or prior to creating percolation zone 220.

Figure 6A:
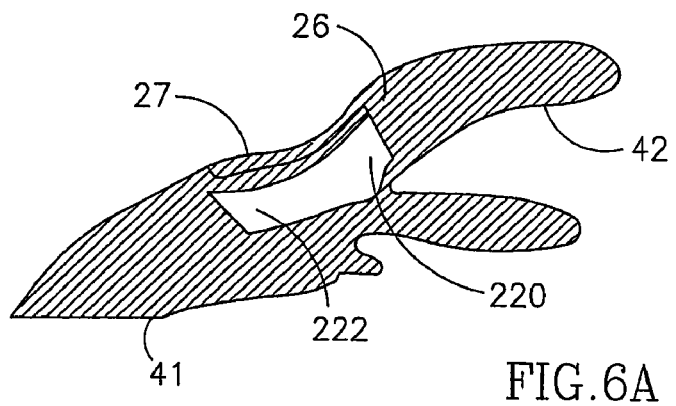
FIGS. 6A and 6B illustrate a completed percolation and reservoir system, from a side and a top view, in accordance with an exemplary embodiment of the invention.
Figure 6B:
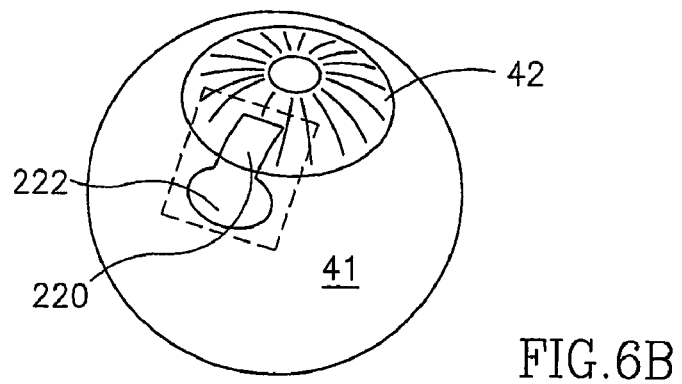

FIGS. 6A and 6B illustrate a completed percolation (220) and reservoir (222) system, from a side and a top view, in accordance with an exemplary embodiment of the invention.

FIG. 6A shows the situation after flaps 26 and 27 are closed. FIG. 6B is a top view, with the flaps shown as a dotted line.

As shown, reservoir 222 and percolation zone 220 have different geometries, which can include different shapes, sizes and/or depths. In an exemplary embodiment, percolation zone 220 is 3×3 mm and reservoir 222 is 5×3 mm. Alternative exemplary sizes for percolation zone 220 are between 2 and 5 mm by between 2 and 5 mm. Alternative exemplary sizes for reservoir 222 are between 3 and 5 mm by between 3 and 5 mm. The actual sizes of the zones may be fixed. Alternatively, one or both sizes decided ahead of time based on patient characteristics, for example, eye-size, age and intra-ocular pressure. Alternatively or additionally, the actual sizes may be decided during the procedure, for example, based on the percolation rate. Alternatively or additionally, the sizes of percolation zone 220 and/or reservoir 222 may be adjusted (up or down) in a later procedure.

However non-rectangular shapes can be provided, for example, round, elliptical or polygonal with, for example, between 3 and 10 facets. In particular, both convex and concave forms may be provided, for example to provide different perimeter-area ratios for reservoir 222 and/or percolation zone 220. Alternatively or additionally, at least part of one of the zones may be provided as a plurality of elongated zones.

Alternatively to contiguous reservoir and percolation zone, the two may be separated by one or more channels, for example a channel ablated in the sclera.

In some cases, ablation may cause charring of the eye or deposition of debris. Optionally, such charring is cleaned away using fluid or a wipe.

Optionally, prior to closing the flaps, a spacer is insert to maintain reservoir 222 and/or percolation zone 220 open (212), at least until the spacer is absorbed, as some spacers are formed of a bio-absorbable material. Exemplary spacers are:

(a) AquaFlow by Staar inc., formed of collagen;

(b) SK-Gel by Corneal Co., formed or reticulated hyaluronic acid;

(c) Hydrogel implants of various designs; and/or (d) Scleral implants formed of left over or harvested pieces of ocular tissue.

Alternatively or additionally to a spacer, an anti-metabolic material may be provided at the ablated area, to retard tissue ingrowth. Exemplary materials include: Mitomycin, typically contact-applied as a damp sponge for 2-3 minutes and 5-Fluoro-Uracil (5FU), typically applied as a series of sub-conjectival injection after the procedure.

At 214, the flaps are closed and sealed, for example using a laser, adhesive or by sewing.

Alternatively to scanning, in one embodiment of the invention, a large spot size is used, to cover the entire ablation area. Optionally, ablation will stop at portions of the ablated area that percolate, for example by a mechanism of the laser light being absorbed by the percolating aqueous humor only at the sufficiently ablated locations.

In another alternative to scanning, the procedure may be performed free-hand. Optionally, an integral scanner is provided in the probe. An aiming beam, which may be scanned or not, may be used to show the scan boundaries.

In an exemplary embodiment of the invention, the self-limiting behavior of the laser interaction with the sclera is used as a control feature or a safety feature, depending on the laser and on the degree of certainty. In one example, the self-limiting behavior is used as a control feature. The laser is set to have an ablation depth (e.g., power, pulse length) equal to the expected percolation rate when a desired membrane is achieved. This percolation rate may depend, for example, on the intra-ocular pressure and/or on other parameters, such as results from a previous or a same operation on the patient. Another possible setting is a matching between ablation depth in sclera and in fluid. This setting may vary, for example, if the sclera or intra-ocular fluid are dyed or otherwise have significantly different absorption at the laser wavelength. Optionally, the scan settings are modified to provide a local pulse rate that matches the expected percolation rate. In an exemplary embodiment of the invention, the power setting is 3 $J/cm^2$ and the pulse duration is 1 ms. Higher power, such as 10 or 20 $J/cm^2$ at this pulse duration will provide a greater ablation depth. Exemplary durations are thus between 1-2000 µs, for an isotopic $CO_2$ laser. Exemplary power levels are between 2.5 and 50 $J/cm^2$. In contrast, an Erbium:YAG can work at 1.5 J, but has undesirable self-limiting behavior. The exact power setting may depend of course on the exact spectral wavelength of the laser and/or on the absorbency characteristics of the sclera. Also, the sclera and/or the percolating fluid (e.g., the eye) may be dyed to have desired absorbency characteristics.

The procedure as described above is applied. Once the percolation is fast enough, the ablation effectively stops and the operator can stop the laser. Alternatively, the automatic vision system is used to stop the procedure once it is determined that no further ablation of sclera is being achieved.

In a safety method, the same setting settings are applied, However, the operator does not trust the system or is worried that thermal damage may be caused by repeated ablation of fluid. Instead, the operator sets the ablation depth and ablates until he sees fluid and then ablates at a slower rate (e.g., using less often applied manual "zap" instructions) and/or at a lower ablation thickness setting, until the percolation rate appears to be correct. If the operator makes a mistake, the ablation should not penetrate through the sclera, as it is self-limiting.

It should be noted that the same procedure, possibly with different parameters may be applied to a wide range of patients. These patients may be characterized, for example, by different percolation rates and/or different target percolation rates. For example, the non-penetrating filtration procedure may be applied as a precautionary measure or in patients with slightly elevated intra-ocular pressures, such as pressures, between 14 mmHg and 21 mmHg or below 30 mmHg.

Figure 7:
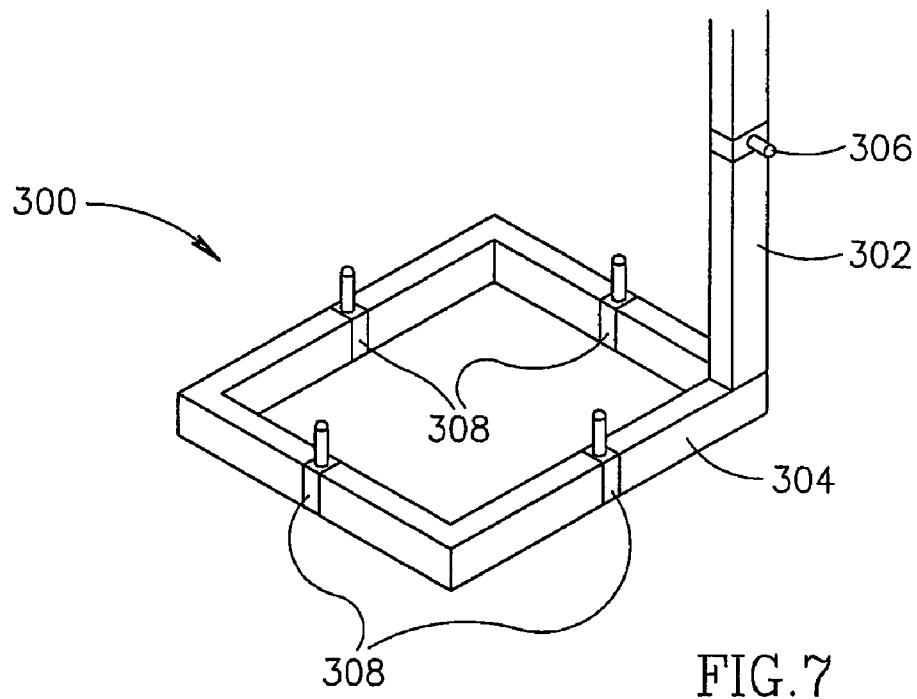
FIG. 7 illustrates an exemplary protective framework, in accordance with an embodiment of the invention.

FIG. 7 illustrates an exemplary protective framework 300, in accordance with an embodiment of the invention. Framework 300 is optionally attached to microscope 58 and blocks laser light from reaching outside of the ablation areas 30 and 31 and/or a safety zone defined around them. Alternatively or additionally, framework 300 may be attached to the patient. As shown, framework 300 comprises an attachment extension 302 for attaching the framework and a frame 304 defined, in this embodiment, by four bars. These bars may be wider than shown and/or may have a curtain attached to them for example a disposable adhesive (to the framework) curtain. The required focal distances of the procedure are optionally set using framework 300. A distance adjustment screw 306 may optionally be provided. Alternatively or additionally, framework geometry defining screws 308 may be provided, to control the shape and/or size of the framework and, thus, the ablateable zone. In some embodiments, frame 300 is not rectangular, for example being formed of a pliable wire. Alternatively or additionally, frame 300 may be semi-transparent, but not to except to beam 54. In one example, frame 700 comprises a holder, for example a clip, for a transparent plate the defines the laser action area.

Figure 8A:
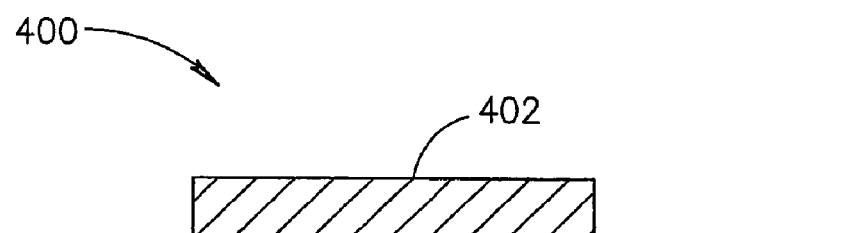
FIGS. 8A and 8B illustrate two alternative exemplary eye protectors in accordance with some embodiments of the invention.
Figure 8B:
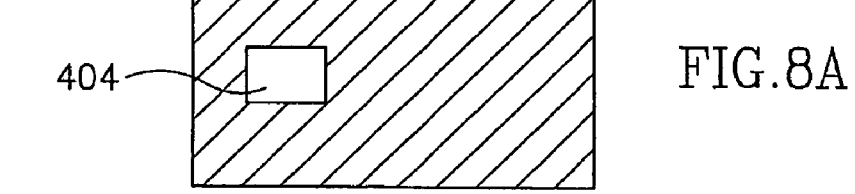

FIGS. 8A and 8B illustrate two alternative exemplary eye protectors in accordance with some embodiments of the invention.

FIG. 8A shows an aperture type protector 400, comprising a body 402 that blocks laser light and an aperture 404 which passes laser light. In one embodiment of the invention, body 402 is flexible and adhesive, for example being a silicon rubber sheet. Optionally, body 402, when attached to eye 40, maintains flaps 26 and 27 open. Alternatively to being flexible, body 402 may be rigid or plastically deformable. Alternatively to adhesive, other attachment methods, such as suturing, vacuum and/or self adhesion to the eye surface based on mechanical properties of the eye surface and/or body 402, may be used instead. Protector 400 may be disposable or sterilizable. Optionally, aperture 404 (or window 410, below) defines the shape of the ablation areas and/or shape of the flaps, for example if the flaps are cut using a laser.

FIG. 8B shows a window type protector 410 having a body 412 which can be the same as body 402. However, instead of an aperture 404, a window 414 may be provided for selective transmission of laser light. As shown, window 414 may protrude, for example towards the microscope, optionally to provide contact with the optical path and/or towards the eye, for example fitting into areas 30 and 31. Alternatively, a flat window may be provided. In an exemplary embodiment of the invention, window 414 is formed of a laser sensitive material, that turn opaque after a certain amount of energy is deposited in it, preventing inadvertent damage to the eye.

Alternatively, protector 410 may be attached to the microscope, for example using adhesive or being formed as a slide that can be coupled to the microscope. Alternatively to a slide, movable shutters are provided to limit the possible positions of the laser beam on the eye.

It will be appreciated that the above described methods of selective ablation of sclera and corneal tissue may be varied in many ways, including, changing the order of steps and the types of tools used. In addition, a multiplicity of various features, both of method and of devices have been described. In some embodiments mainly methods are described, however, also apparatus adapted for performing the methods are considered to be within the scope of the invention. It should be appreciated that different features may be combined in different ways. In particular, not all the features shown above in a particular embodiment are necessary in every similar embodiment of the invention. Further, combinations of the above features are also considered to be within the scope of some embodiments of the invention. Also within the scope of the invention are surgical kits which include sets of medical devices suitable for performing a single or a small number filtration procedures. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

The invention claimed is:

1. A method of performing a non-penetrating filtration procedure, comprising:
   (a) opening a flap in an eye, overlying a Schlemm's canal of said eye;
   (b) forming a percolation zone adjacent said Schlemm's canal by:
      (i) removing, by ablation with a laser, a tissue thickness of between 5 and 50 microns, at a time; and
      (ii) repeating said removing after a delay sufficient to detect percolation, said removing being repeated until sufficient percolation is achieved and without penetrating into a body of said eye;
   (c) closing said flap.

2. A method according to claim 1, wherein forming a percolation zone comprises cleaning away charred tissue from said percolation zone.

3. A method according to claim 1, wherein forming a percolation zone comprises forming by automatic scanning with a laser.

4. A method according to claim 3, wherein automatic scanning with a laser comprises automatically controlling at least one parameter of the scanning responsive to an effect of the laser on the tissue.

5. A method according to claim 3, wherein said laser is a pulsed laser configured to provide multiple pulses during the scanning of a point.

6. A method according to claim 1, wherein said laser is a $CO_2$ laser.

7. A method according to claim 6, wherein said laser is a $^{13}C^{16}O_2$ laser.

8. A method according to claim 1, wherein said laser is an Er:YSGG laser.

9. A method according to claim 1, wherein said laser is a diode laser operated near 1.8 microns wavelength.

10. A method according to claim 1, comprising placing a protective sticker on said eye prior to forming said percolation zone, said protective sticker having a spatial window that admits a wavelength of said laser and a body that block said wavelength from parts of the eye other than an area to be ablated.

11. A method according to claim 1, wherein said laser has a dwell time for said removing of over 100 micro seconds.

12. A method according to claim 1, wherein said laser has a spot size of over 100 microns.

13. A method according to claim 1, wherein each tissue removing has a duration of over 1 milliseconds.

14. A method according to claim 1, wherein said forming includes removing in a concave pattern.

15. A method according to claim 1, wherein said removing comprises removing between 10 and 30 microns at a time.

16. A method according to claim 1, wherein said removing comprises removing between 16 and 25 microns at a time.

17. A method according to claim 1, wherein said removing comprises removing between 16 and 20 microns at a time.

18. A method according to claim 1, wherein said removing comprises removing between 5 and 30 microns at a time.

19. A method according to claim 1, comprising forming a reservoir in a sclera of said eye and in fluid connection with said percolation zone.

20. A method according to claim 1, wherein said laser is a continuous laser.

* * * * *